US010340118B2

(12) United States Patent
Sagawa

(10) Patent No.: US 10,340,118 B2
(45) Date of Patent: Jul. 2, 2019

(54) SCANNING TRANSMISSION ELECTRON MICROSCOPE AND METHOD OF IMAGE GENERATION

(71) Applicant: JEOL Ltd., Tokyo (JP)

(72) Inventor: Ryusuke Sagawa, Tokyo (JP)

(73) Assignee: JEOL Ltd., Tokyo (JP)

(*) Notice: Subject to any disclaimer, the term of this patent is extended or adjusted under 35 U.S.C. 154(b) by 0 days.

(21) Appl. No.: 15/824,047

(22) Filed: Nov. 28, 2017

(65) Prior Publication Data
US 2018/0337019 A1 Nov. 22, 2018

(30) Foreign Application Priority Data

Nov. 28, 2016 (JP) .................................. 2016-230168

(51) Int. Cl.
*H01J 37/28* (2006.01)
*G01N 23/20058* (2018.01)
(Continued)

(52) U.S. Cl.
CPC ........ *H01J 37/28* (2013.01); *G01N 23/20058* (2013.01); *H01J 37/10* (2013.01);
(Continued)

(58) Field of Classification Search
CPC .... H01J 37/10; H01J 37/1475; H01J 37/1477; H01J 37/244; H01J 37/265; H01J 37/28; H01J 2237/2802; H01J 2237/2803
See application file for complete search history.

(56) References Cited

U.S. PATENT DOCUMENTS 4,514,629 A * 4/1985 Smith .................... H01J 37/22
250/311
5,004,918 A * 4/1991 Tsuno ................... H01J 37/222
250/307

(Continued)

FOREIGN PATENT DOCUMENTS

JP        2005235665 A       9/2005

OTHER PUBLICATIONS

European Search Report dated Mar. 28, 2018 in EP application No. 17204093.

*Primary Examiner* — David E Smith
(74) *Attorney, Agent, or Firm* — The Webb Law Firm

(57) ABSTRACT

There is provided a scanning transmission electron microscope capable of producing plural types of STEM (scanning transmission electron microscopy) images using a single detector. The electron microscope (100) has an electron source (10) emitting an electron beam, a scanning deflector (13) for scanning the beam over a sample (S), an objective lens (14) for focusing the beam, an imager (22) placed at a back focal plane of the objective lens (14) or at a plane conjugate with the back focal plane, and a scanned image generator (40) for generating scanned images on the basis of images captured by the imager. The scanned image generator (40) operates to form electron diffraction patterns from the electron beam passing through positions on the sample by the scanning of the electron beam, to capture the electron diffraction patterns by the imager so that plural images are produced, to integrate the intensity of each pixel over an integration region that is set based on the size of an image of a transmitted wave in a respective one of the produced images for each of the produced images such that the signal intensity at each position on the sample is found, and to (Continued)

generate the scanned images on the basis of the signal intensities at the positions on the sample.

14 Claims, 17 Drawing Sheets

(51) Int. Cl.
*H01J 37/244* (2006.01)
*H01J 37/10* (2006.01)
*H01J 37/147* (2006.01)
*H01J 37/26* (2006.01)

(52) U.S. Cl.
CPC ...... *H01J 37/1475* (2013.01); *H01J 37/1477* (2013.01); *H01J 37/244* (2013.01); *H01J 37/265* (2013.01); *G01N 2223/0565* (2013.01); *G01N 2223/102* (2013.01); *G01N 2223/3302* (2013.01); *G01N 2223/418* (2013.01); *H01J 2237/2446* (2013.01); *H01J 2237/2802* (2013.01); *H01J 2237/2803* (2013.01)

(56) References Cited

U.S. PATENT DOCUMENTS

| | | | | |
|---|---|---|---|---|
| 2009/0242792 | A1* | 10/2009 | Hosoya | H01J 37/222 250/397 |
| 2013/0043386 | A1* | 2/2013 | Yamazaki | H01J 37/28 250/307 |
| 2013/0062520 | A1* | 3/2013 | Henstra | H01J 37/153 250/311 |

\* cited by examiner

SCANNING TRANSMISSION ELECTRON MICROSCOPE AND METHOD OF IMAGE GENERATION

BACKGROUND OF THE INVENTION

Field of the Invention

The present invention relates to a scanning transmission electron microscope and method of image generation.

Description of Related Art

A scanning transmission electron microscope (STEM) is an instrument for obtaining a scanning transmission electron microscope (STEM) image by scanning a focused electron beam (electron probe) over a sample and detecting electrons transmitted through the sample (see, for example, JP-A-2005-235665).

In a scanning transmission electron microscope, STEM images have been generated by integrating the signal intensity of the electron beam over a certain region of an electron diffraction pattern created at the back focal plane of the objective lens by the use of a detector that is configured including a scintillator and a photomultiplier tube. The certain region assumes a disk-like form or annular form which is determined by the shape of the scintillator. Such a scanning transmission electron microscope can produce general STEM images and various other STEM images such as annular bright-field STEM images, low-angle dark-field STEM images, and high-angle dark-field STEM images, depending on the scintillator shape.

When two types of STEM images, for example, are obtained with a conventional scanning transmission electron microscope, however, two types of detectors must be prepared. In this way, with the conventional scanning transmission electron microscope, plural detectors must be prepared in order to produce plural types of STEM images.

SUMMARY OF THE INVENTION

The present invention has been made in view of the foregoing problem. One object associated with some aspects of the present invention is to provide a scanning transmission electron microscope which can produce plural types of STEM images using only one detector. Another object associated with some aspects of the invention is to provide a method of image generation capable of generating plural types of STEM images using only one detector.

(1) A scanning transmission electron microscope associated with the present invention is adapted to obtain scanned images by scanning an electron beam over a sample. The scanning transmission electron microscope has: an electron source for emitting an electron beam; a scanning deflector for scanning the emitted electron beam over the sample; an objective lens for converging the electron beam emitted from the electron source; an imager located at a back focal plane of the objective lens or at a plane conjugate with the back focal plane; and a scanned image generator for generating the scanned images on the basis of images captured by the imager. The scanned image generator operates to form electron diffraction patterns from the electron beam passing through positions on the sample by scanning of the electron beam, to capture the electron diffraction patterns by the imager so that plural images are produced, to integrate the intensity of each pixel over an area (hereinafter may be referred to as the integration region) that is set based on the size of an image of a transmitted wave within a respective one of the produced images such that the signal intensity at each position on the sample is found for each of the produced images, and to generate the scanned images on the basis of the signal intensities at the positions on the sample.

In this scanning transmission electron microscope, various types of scanned images can be generated according to the purpose of observation or analysis and according to the integration regions. Consequently, this microscope can provide plural types of scanned images using only one detector or imager.

(2) In one feature of the scanning transmission electron microscope of (1) above, the image of the transmitted wave in the image captured by the imager may appear as a disk. The size of the image of the transmitted wave may be the diameter of the disk.

(3) In one feature of the scanning transmission electron microscope of (1) or (2) above, the scanned image generator may operate to measure the size of the image of the transmitted wave from the image captured by the imager and to set the integration region on the basis of the measured size of the image of the transmitted wave.

(4) In one feature of the scanning transmission electron microscope of any one of (1)-(3) above, during the operation for finding the signal intensity at each position on the sample, the scanned image generator may find the signal intensity at each position on the sample for each of the plural set integration regions. During the operation for generating the scanned images, the scanned image generator may generate the scanned images corresponding to the integration regions.

In this scanning transmission electron microscope, plural types of scanned images can be generated according to the plural integration regions. Consequently, this microscope can generate plural types of scanned images simultaneously from plural images, which in turn are produced by capturing the electron diffraction patterns by means of the imager, the patterns being created by the electron beam passing through positions on the sample.

(5) In one feature of the scanning transmission electron microscope of any one of (1)-(4) above, the integration regions may be inside the image of the transmitted wave and be circular regions whose centers lie at the center of the image of the transmitted wave.

This scanning transmission electron microscope can generate bright-field STEM images.

(6) In another feature of the scanning transmission electron microscope of any one of (1)-(4) above, the integration regions may be inside the image of the transmitted wave and be annular regions whose centers lie at the center of the image of the transmitted wave.

This scanning transmission electron microscope can generate annular bright-field STEM images.

(7) In a further feature of the scanning transmission electron microscope of any one of (1)-(4) above, the integration regions are outside and surround the image of the transmitted wave and are annular regions whose centers lie at the center of the image of the transmitted wave.

This scanning transmission electron microscope can generate annular dark-field STEM images.

(8) In a yet other feature of the scanning transmission electron microscope of any one of (1)-(4) above, the integration regions may be inside the image of the transmitted wave and be two regions which are symmetrical with respect to the center of the image of the transmitted wave.

This scanning transmission electron microscope can generate differential phase contrast STEM images.

(9) In a yet other feature of the scanning transmission electron microscope of any one of (1)-(8) above, there may be further included: a first deflector for deflecting the electron beam incident on the sample; a second deflector for deflecting the electron beam incident on the imager; and a processor for controlling the first and second deflectors. The processor may operate to control the first deflector such that the azimuthal angle of the electron beam incident on the sample is scanned, to obtain an accumulation image consisting of an accumulation of images each containing a transmitted wave and diffracted waves in a respective one of electron diffraction patterns produced at different values of the azimuthal angle, to extract the image of the transmitted wave from the accumulation image, and to control the second deflector on the basis of the position of the extracted image of the transmitted wave such that the image of the transmitted wave is placed at the center of the image captured by the imager.

In this scanning transmission electron microscope, the image of the transmitted wave is located at the center of the image captured by the imager and so the size of the image of the transmitted wave within the image captured by the imager can be measured easily.

(10) A method of generating images in accordance with the present invention is implemented to produce scanned images in a scanning transmission electron microscope by scanning an electron beam incident on a sample. This method starts with forming electron diffraction patterns from the electron beam that is caused to pass through positions on the sample by the scanning of the electron beam. The electron diffraction patterns are captured by an imager to thereby produce plural images. The intensity of each pixel within an integration region that is set based on the size of an image of a transmitted wave in a respective one of the produced images is integrated for each of the produced images to find the signal intensity at each position on the sample. The scanned images are generated based on the signal intensities at the positions on the sample.

In this method of image generation, various types of scanned images can be generated according to the integration regions and according to the purpose of observation or analysis. Therefore, with this method, it is possible to produce plural types of scanned images using only one detector or imager.

DESCRIPTION OF THE INVENTION

The preferred embodiments of the present invention are hereinafter described in detail with reference to the drawings. It is not intended that the embodiments provided below unduly restrict the scope and content of the present invention delineated by the appended claims. Also, it is to be understood that not all the configurations described below are essential constituent components of the invention.

1. First Embodiment

1.1. Scanning Transmission Electron Microscope

Figure 1:
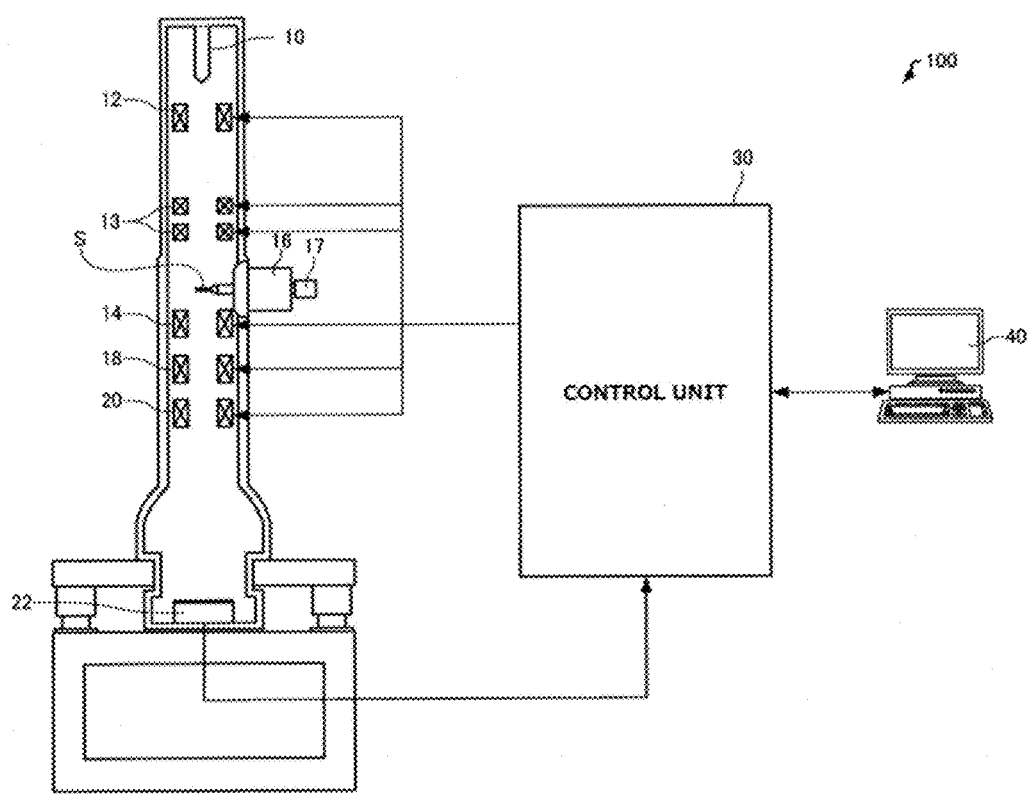
FIG. 1 is a schematic diagram, partly in cross section, of a scanning transmission electron microscope associated with a first embodiment of the present invention.

A scanning transmission electron microscope associated with a first embodiment of the present invention is first described by referring to FIG. 1, which schematically shows the scanning transmission electron microscope, 100, associated with the first embodiment.

The scanning transmission electron microscope 100 is an instrument for producing a scanned image, which may be hereinafter also referred to as a STEM (scanning transmission electron microscopy) image, by scanning an electron probe (that is a focused electron beam) over a sample S and detecting electrons transmitted through the sample S.

As also shown in FIG. 1, the scanning transmission electron microscope 100 includes an electron source 10, a condenser lens system 12, scan coils 13 being one example of scanning deflector, an objective lens 14, a sample stage 16, a sample holder 17, an intermediate lens 18, a projector lens 20, an imager 22, a control unit 30, and a personal computer (PC) 40 being one example of scanned image generator.

The electron source 10 emits an electron beam. For example, the electron source 10 is an electron gun which emits the electron beam by accelerating electrons, released from a cathode, by means of an anode.

The condenser lens system 12 focuses the electron beam produced from the electron source 10. The condenser lens system 12 may be composed of a plurality of electron lenses (not shown).

The scan coils 13 are used to deflect the electron beam in two dimensions such that the electron beam (electron probe) focused by the condenser lens system 12 and objective lens 14 is scanned over the sample S.

The objective lens 14 is used to focus the electron beam onto the sample S for forming the electron probe. Also, the objective lens 14 images the electrons transmitted through the sample S. An electron diffraction pattern is formed at the back focal plane of the objective lens 14.

The scanning transmission electron microscope 100 also includes an illumination system (not shown) which incorporates a condenser aperture for controlling the angular aperture and dose of the electron beam.

The sample stage 16 holds the sample S. In the illustrated example, the sample stage 16 holds the sample S via the sample holder 17. The sample stage 16 can move the sample S horizontally and vertically and tilt the sample S.

The intermediate lens 18 and projector lens 20 operate as transfer lenses for magnifying and transferring the electron diffraction pattern formed at the back focal plane of the objective lens 14.

The imager 22 is placed in a plane conjugate with the back focal plane of the objective lens 14. In the scanning transmission electron microscope 100, the intermediate lens 18 and projector lens 20 cooperate to magnify and transfer the back focal plane of the objective lens 14. As a result, a plane conjugate with the back focal plane is formed in the photosensitive area of the imager 22. Consequently, the imager 22 can capture the electron diffraction pattern. Alternatively, the imager 22 may be placed at the back focal plane of the objective lens 14.

The imager 22 is a digital camera capable of recording the electron diffraction pattern as a two-dimensional digital image. For example, the imager 22 is a pixelated STEM detector, which is a high speed image sensor capable of detecting the electron beam in two dimensions and obtaining a two-dimensional image. Furthermore, the high speed image sensor can follow the scanning of the electron beam.

The center of the photosensitive area of the imager 22 (i.e., the center of the sensor) is located on the optical axis of the optical system of the scanning transmission electron microscope 100. Furthermore, the center of the photosensitive area of the imager 22 corresponds to the center of the image captured by the imager 22.

The control unit 30 controls the component parts 10, 12, 13, 14, 18, 20, and 22 of the scanning transmission electron microscope 100 on the basis of control signals from the PC 40. The functions of the control unit 30 may be implemented by dedicated circuitry or executing computer programs using a processor such as a CPU.

The personal computer 40 performs various operations including an operation for generating control signals for controlling the various component parts of the scanning transmission electron microscope 100 and an operation for generating various STEM images on the basis of the image captured by the imager 22.

The personal computer 40 is configured including a manual control unit, a display device, a storage section, and a processing section (none of which are shown). The manual control unit is a device for detecting and entering input information from a user, and outputs the user's input information to the processing section. The function of the manual control unit can be implemented by input devices such as a touch panel display, a touch pad, a mouse, direction keys, buttons, and a keyboard. The image generated by the processing section is input to the display device. The function of the display device can be implemented by an LCD, CRT, touch panel, or other display unit. The storage section stores programs and various types of data for permitting a computer to operate as various parts of the processing section (scanned image generator). Also, the storage section operates as a working area of the processing section. The function of the storage section can be implemented by a hard disk, RAM, or the like. The processing section performs various operations including an operation for generating control signals for controlling the various component parts of the scanning transmission electron microscope 100 and an operation for generating various types of STEM images. The functions of the processing section can be implemented by running programs using various processors such as a CPU.

1.2. Method of Image Generation (1) Technique

A technique of generating a STEM image in the scanning transmission electron microscope associated with the first embodiment is next described.

The method of image generation associated with the present embodiment involves the steps of: scanning an electron beam over the sample S, forming electron diffraction patterns from the electron beam passing through positions on the sample S, capturing the electron diffraction patterns by the imager 22, thus producing plural images; integrating the intensity of each pixel of the produced images over an integration region set based on the size of an image of a transmitted wave within a respective one of the produced images for each of the produced images to find the signal intensity at each position on the sample S; and generating STEM images on the basis of the signal intensities at the positions on the sample S.

Figure 2:
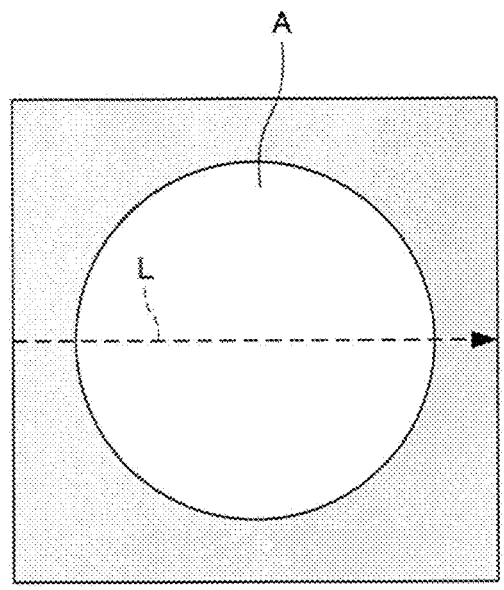
FIG. 2 schematically shows an image of an electron diffraction pattern captured by an imager.

First, an electron diffraction pattern captured by the imager 22 of the scanning transmission electron microscope 100 is first described. FIG. 2 is a schematic diagram of an image of an electron diffraction pattern captured by the imager 22.

In the scanning transmission electron microscope 100, a conically converged electron beam is made to impinge on the sample S and so an electron diffraction pattern in which transmitted and diffracted waves are spread like disks is formed at the back focal plane of the objective lens 14. The electron diffraction pattern formed at the back focal plane of the objective lens 14 is transferred and magnified by the intermediate lens 18 and projector lens 20 and captured by the imager 22. In this way, the electron diffraction pattern shown in FIG. 2 is captured. In this captured image, a disk of a transmitted wave (may be hereinafter also referred to as the transmission disk) appears as an image of the transmitted wave. Also, disks of diffraction waves (may be hereinafter also referred to as the diffraction disks) appear as images of the diffracted waves. Note that only the transmission disk A within the image captured by the imager 22 is shown in FIG. 2 and that the center of the image and the center of the transmission disk A are coincident with each other in FIG. 2.

Figure 3:
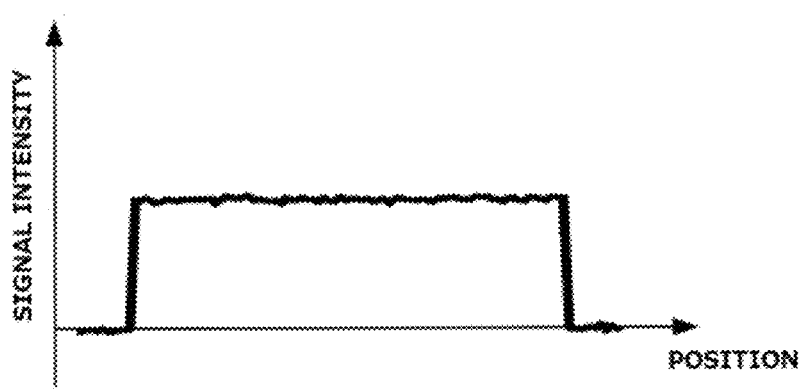
FIG. 3 is a graph of an intensity profile taken along a straight line passing through the center of a transmission disk.
Figure 4:
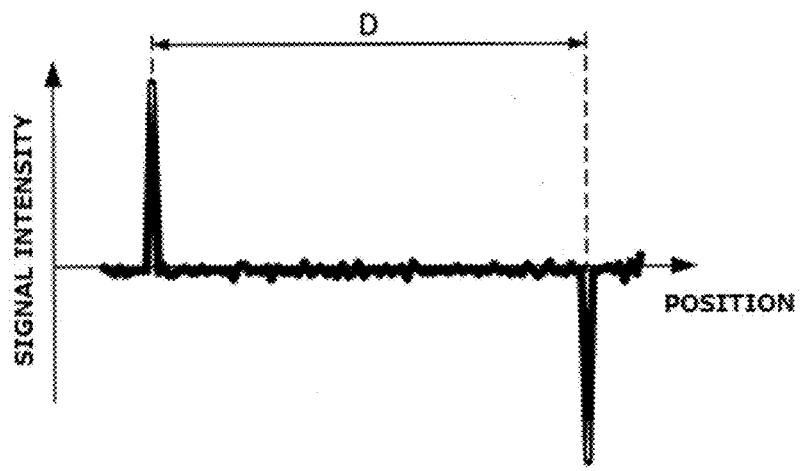
FIG. 4 is a graph illustrating the result of a differentiation of the intensity profile.

A technique of finding the diameter of the transmission disk A (i.e., the size of the transmission disk) is next described. FIG. 3 is a graph showing an intensity profile taken along a straight line L passing through the center of the transmission disk A shown in FIG. 2. FIG. 4 is a graph showing the result of a differentiation of the intensity profile of FIG. 3.

As shown in FIGS. 3 and 4, the diameter of the transmission disk A (i.e., the magnitude of the transmitted wave) can be found by taking the intensity profile along the straight line L passing through the center of the transmission disk A. In the graph showing the result of a differentiation of the intensity profile of FIG. 4, the signal intensity increases at the edges of the transmission disk A. Therefore, the edges of the transmission disk can be detected from the graph showing the result of the differentiation of the intensity profile shown in FIG. 4 by setting a threshold value to a given intensity (absolute value). Thus, the diameter D of the transmission disk can be found.

The technique of finding the diameter of the transmission disk A is not limited to the foregoing method. For example, the diameter of the transmission disk A may be found by detecting a circular disk from the image shown in FIG. 2 by the use of a Hough transform and finding the diameter of the detected circular disk.

Figure 5:
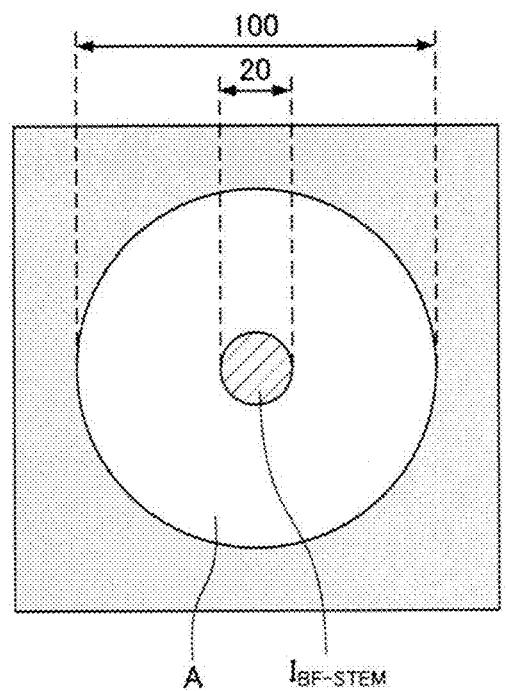
FIG. 5 shows one example of integration region for generating a bright-field STEM image.
Figure 6:
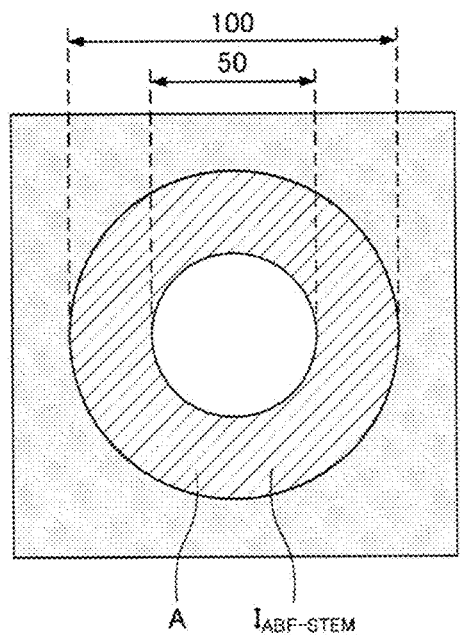
FIG. 6 shows one example of integration region for generating an annular bright-field STEM image.
Figure 7:
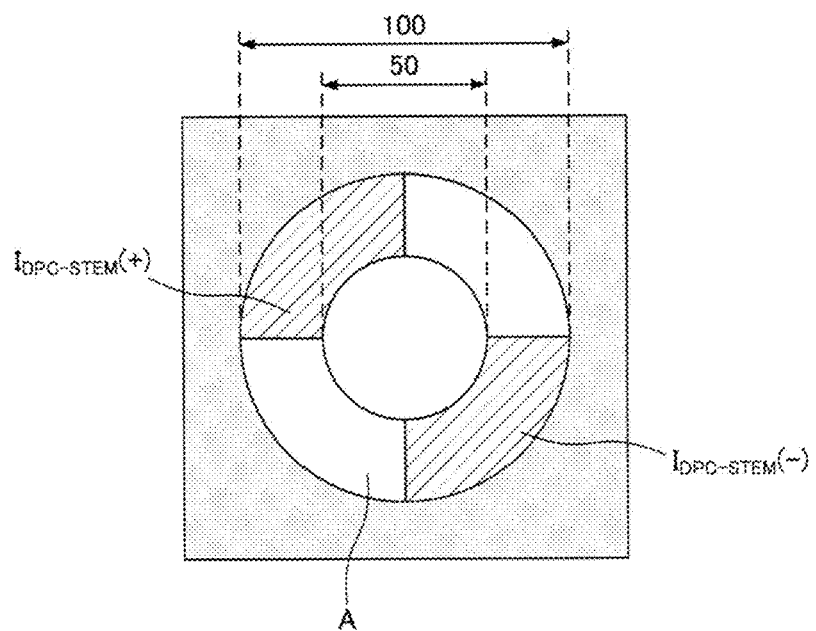
FIG. 7 shows one example of integration region for generating a differential phase contrast STEM image.
Figure 8:
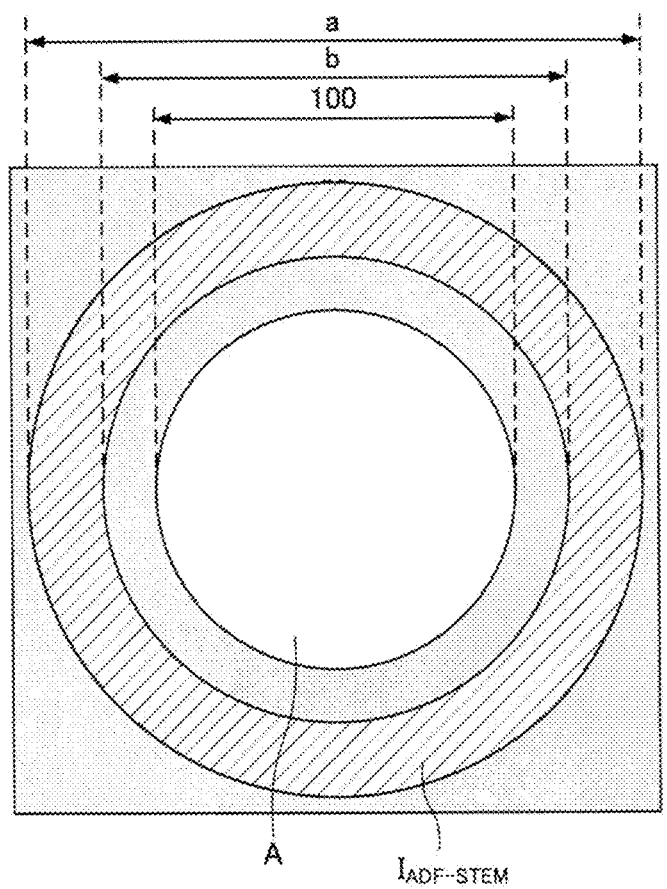
FIG. 8 shows an integration region for generating an annular dark-field STEM image.

Integration regions are next described. FIG. 5 illustrates one example of integration region, $I_{BF-STEM}$, for generating a bright-field STEM image. FIG. 6 illustrates one example of integration region, $I_{ABF-STEM}$, for generating an annular bright-field STEM image. FIG. 7 illustrates one example of a pair of integration regions, $I_{DPC-STEM}$ (+) and $I_{DPC-STEM}$ (−), for generating a differential phase contrast STEM image. FIG. 8 illustrates an integration region $I_{ADF-STEM}$ for generating an annular dark-field STEM image.

A bright-field (BF) STEM (scanning transmission electron microscopy) image is a STEM image constructed by detecting electrons which are transmitted through the sample S without scattering. Where a bright-field STEM image is created, the integration region $I_{BF-STEM}$ is set inside the transmission disk A and in a circular region whose center is at the center of the transmission disk A as shown in FIG. 5.

In the example shown in FIG. 5, the transmission disk A is a circle which is centered at the center of the image and which has a diameter of 100 pixels. The integration region $I_{BF-STEM}$ is set in a circle whose center is at the center of the image and which has a diameter of 20 pixels.

By predetermining the ratio of the diameter of the integration region $I_{BF-STEM}$ to the diameter of the transmission disk A (20/100 in the example of FIG. 5), the integration region $I_{BF-STEM}$ can be set from the measured diameter of the transmission disk A during generation of a bright-field (BF) STEM image.

An annular bright-field (ABF) STEM image is a STEM image constructed by detecting electrons which are transmitted through the sample S and which are scattered at low angles in the bright-field region. When an annular bright-field STEM image is generated, the integration region $I_{ABF-STEM}$ is set inside the transmission region A and in an annular region whose center is at the center of the transmission disk A as shown in FIG. 6.

In the example shown in FIG. 6, the transmission disk A is a circle whose center is at the center of the image and which has a diameter of 100 pixels. The integration region $I_{ABF-STEM}$ is an annular region produced by removing a circle whose center is at the center of the transmission disk A and which has a diameter of 50 pixels from a circle whose center lies at the center of the image and which has a diameter of 100 pixels.

By predetermining the ratio of the diameter of the region inside the integration region $I_{ABF-STEM}$ to the diameter of the transmission disk A (50/100 in the example of FIG. 6), the integration region $I_{ABF-STEM}$ can be set from the measured diameter of the transmission disk A during generation of an ABF-STEM image.

A differential phase contrast STEM image is a STEM image generated by measuring the deflection of an electron beam caused in the sample S by an electromagnetic field at each position in the sample S and visualizing the electromagnetic field. When a differential phase contrast STEM image is generated, a pair of integration regions, $I_{DPC-STEM}$ (+) and $I_{DPC-STEM}$ (−), is set. These two integration regions are symmetrical with respect to the center of the transmission disk A. The amount and direction of the deflection of the electron beam in the sample S can be detected by taking the difference between the integration region $I_{DPC-STEM}$ (+) and the integration region $I_{DPC-STEM}$ (−).

In the example shown in FIG. 7, the transmission disk A is a circle whose center is at the center of the image and which has a diameter of 100 pixels. Each of the integration regions $I_{DPC-STEM}$ (+) and $I_{DPC-STEM}$ (−) is a circular sector with a central angle of 90 degrees produced by removing a circle whose center is at the center of the image and which has diameter of 50 pixels from a circle whose center is at the center of the image and which has a diameter of 100 pixels. These two integration regions are arranged symmetrically with respect to the center of the image.

By predetermining the ratio of the diameter of the region inside the integration regions $I_{DPC-STEM}$ (+) and $I_{DPC-STEM}$ (−) to the diameter of the transmission disk A (50/100 in the example of FIG. 7), the integration regions $I_{DPC-STEM}$ (+) and $I_{DPC-STEM}$ (−) can be set from the measured diameter of the transmission disk A during generation of a differential phase contrast (DPC) STEM image.

An annular dark-field (ADF) STEM image is a STEM image constructed by detecting those electrons of the electron beam transmitted through the sample S which are scattered or diffracted. When an annular dark-field STEM image is generated, the integration region $I_{DPC-STEM}$ is set in an annular region which is outside and around the transmission region A and whose center is at the center of the transmission disk A as shown in FIG. 8.

In the example shown in FIG. 8, the transmission disk A is a circle whose center is at the center of the image and which has a diameter of 100 pixels. The integration region $I_{ADF-STEM}$ is an annular region produced by removing a circle whose center is at the center of the image and which has a diameter of b pixels from a circle whose center lies at the center of the image and which has a diameter of a pixels (a>b>100 pixels).

By predetermining the ratio of the inside diameter of the integration region $I_{ADF-STEM}$ to the diameter of the transmission disk A (b/100 in the example of FIG. 8) and the ratio of the outside diameter of the integration region $I_{ADF-STEM}$ to the diameter of the transmission disk A (a/100 in the example of FIG. 8), the integration region $I_{ADF\text{-}STEM}$ can be set from the measured diameter of the transmission disk A during generation of an annular differential phase STEM image.

For example, when the integration region $I_{ADF\text{-}STEM}$ is set, a low-angle annular dark-field scanning transmission electron microscopy (LAADF-STEM) image and a high-angle annular dark-field scanning transmission electron microscopy (HAADF-STEM) image can be generated by appropriately adjusting the numbers of pixels a and b. A low-angle annular dark-field STEM image is a STEM image generated by detecting electrons diffracted at low angles and electrons inelastically scattered at low angles from an annular dark-field STEM image. A high-angle annular dark-field STEM image is a STEM image generated by detecting electrons inelastically scattered at high angles from an annular dark-field STEM image.

All of the above-described integration regions $I_{BF\text{-}STEM}$, $I_{ABF\text{-}STEM}$, $I_{DPC\text{-}STEM}$ (+), $I_{DPC\text{-}STEM}$ (−), and $I_{ADF\text{-}STEM}$ can also be set based on the diameter of the transmission disk A. Therefore, in the scanning transmission electron microscope 100, information (e.g., in the case of a bright-field-STEM image, the ratio of the diameter of the integration region $I_{BF\text{-}STEM}$ to the diameter of the transmission disk A) for setting the integration regions $I_{BF\text{-}STEM}$, $I_{ABF\text{-}STEM}$, $I_{DPC\text{-}STEM}$ (+), $I_{DPC\text{-}STEM}$ (−), and $I_{ADF\text{-}STEM}$ is previously stored in the storage section of the personal computer 40. The PC 40 reads out the information according to the type of the STEM image and sets an integration region from the measured diameter of the transmission disk A, the integration region corresponding to the type of a STEM image to be generated.

In the foregoing example, the diameter of the transmission disk A is used as the size of the transmission disk A but the size is not limited to this dimension. The radius or area of the transmission disk A may be used as the size of the transmission disk.

A technique of generating a STEM image is next described. In the scanning transmission electron microscope 100, an image containing a transmission disk within an electron diffraction pattern can be obtained at each position on the sample S by capturing the electron diffraction pattern formed from an electron beam passing through each position on the sample S with the imager 22.

Specifically, in the scanning transmission electron microscope 100, the electron beam emitted from the electron source 10 is conically focused onto the sample S by the condenser lens system 12 and objective lens 14. Consequently, the electron beam transmitted through the sample S forms an electron diffraction pattern at the back focal plane of the objective lens 14. Because the electron beam is scanned over the sample S by the scan coils 13, the imager 22 can capture the electron diffraction pattern formed from electrons passing through positions on the sample S.

Figure 9:
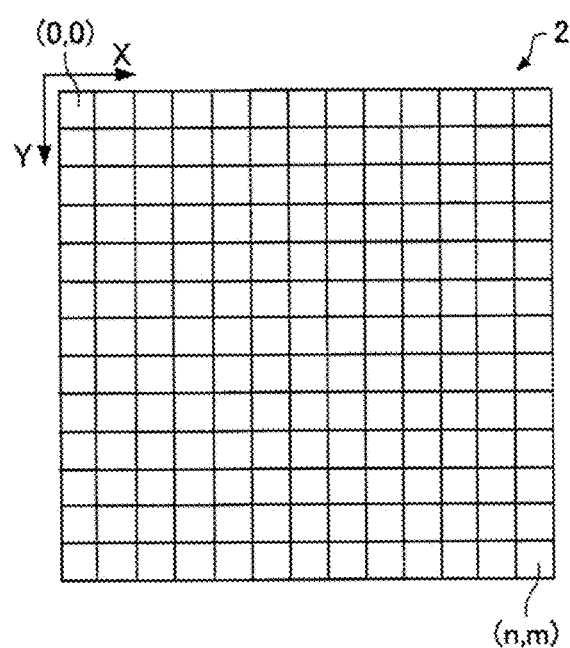
FIG. 9 illustrates a STEM image.

FIG. 9 illustrates STEM image 2 which is composed of n×m pixels (where n and m are arbitrary integers). As described previously, an image of an electron diffraction pattern corresponding to pixels on the STEM image 2 can be obtained by capturing the electron diffraction pattern by the imager 22, the pattern being formed by the electron beam passing through the positions on the sample S. In the example shown in FIG. 9, an image of the electron diffraction pattern of n×m pixels corresponding to pixels (X, Y)=(0, 0), (1, 0), (2, 0), . . . , (n, m) is derived.

For example, where a bright-field STEM image is generated, the intensity value of each pixel within the integration region $I_{BF\text{-}STEM}$ of the image of the electron diffraction pattern consisting of the n×m pixels is integrated, and the resulting integrated value is taken as the signal intensity of a respective pixel in the STEM image 2. The gray scale levels of the pixels are set according to the obtained signal intensities of the pixels of the STEM image 2. In consequence, a bright-field STEM image is generated. An annular bright-field STEM image and an annular dark-field STEM image can be similarly generated.

Where a differential phase contrast STEM is produced, the intensity value of each pixel within each of the integration regions $I_{DPC\text{-}STEM}$ (+) and $I_{DPC\text{-}STEM}$ (−) of the image of the electron diffraction pattern consisting of n×m pixels is integrated. The difference between the two integrated values is calculated. The difference is taken as the signal intensity at a respective pixel in the STEM image 2.

The technique of generating bright-field STEM image, annular bright-field STEM image, differential phase contrast STEM image, and annular dark-field STEM image has been described thus far. In the present embodiment, integration regions can be set at will. Accordingly, in the present embodiment, various types of STEM images can be generated according to the purpose of observation or analysis.

(2) Operation of Scanning Transmission Electron Microscope

Figure 10:
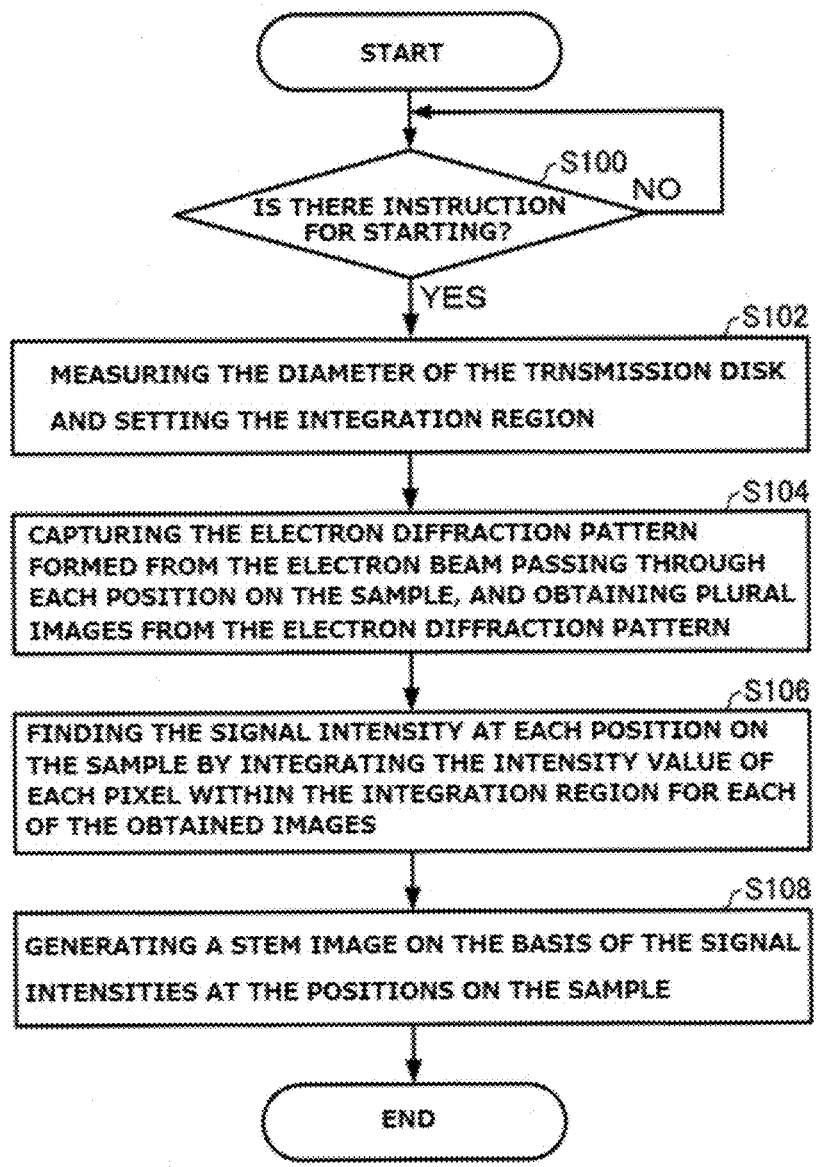
FIG. 10 is a flowchart illustrating one example of operational sequence of the scanning transmission electron microscope of FIG. 1.

The operation of the electron microscope associated with the first embodiment is next described. Here, an operation for generating a STEM image in the scanning transmission electron microscope 100 is described. FIG. 10 is a flowchart illustrating one example of operational sequence of the scanning transmission electron microscope 100 associated with the first embodiment.

First, the personal computer (processing section) 40 makes a decision as to whether the user has issued an instruction for starting acquisition of a STEM image (step S100). The PC 40 determines that the user has issued such an instruction for starting acquisition of a STEM image, for example, if the user has performed a manipulation for starting the acquisition using the STEM image acquisition starting button, the keyboard, a GUI, or the like. At this time, the user issues an instruction to select the type of STEM image together with the instruction for starting the acquisition of the STEM image. A case in which the user selects a bright-field STEM image is hereinafter described.

If the decision at step S100 is YES, indicating that an instruction for starting acquisition of a STEM image is issued, the PC 40 (processing section) measures the diameter of the transmission disk within the image captured by the imager 22 and sets the integration region $I_{BF\text{-}STEM}$ on the basis of the measured diameter of the disk (step S102).

In particular, the PC 40 obtains an image of the electron diffraction pattern captured by the imager 22 and measures the diameter of the transmission disk from the image. This image is obtained, for example, by capturing the electron diffraction pattern formed by the electron beam passing through arbitrary positions on the sample S. As mentioned above, the diameter of the transmission disk may be measured by taking an intensity profile along a straight line passing through the center of the transmission disk or by using a Hough transform.

The PC 40 sets the integration region $I_{BF\text{-}STEM}$ based on the measured diameter of the transmission disk. The PC 40 reads information about the ratio (20/100 in the example of FIG. 5) of the diameter of the integration region $I_{BF\text{-}STEM}$ to the diameter of the transmission disk A from the storage section. The integration region $I_{BF\text{-}STEM}$ is set by multiplying the measured diameter of the transmission disk by this ratio. In this way, in the scanning transmission electron microscope 100, when the user selects the type of STEM image, the integration region can be automatically set.

Then, the electron diffraction pattern formed from the electron beam passing through each position on the sample S by scanning of the beam is captured by the imager 22, and the PC 40 (processing section) obtains plural images from the electron diffraction pattern (step S104).

In particular, the PC 40 controls the scan coils 13 such that the electron beam is scanned over the sample S. Thus, the electron beam is scanned over the sample S, and the electron diffraction pattern formed from the electron beam passing through positions on the sample S is captured by the imager 22. The images of the electron diffraction pattern at the positions on the sample S captured by the imager 22 are sent to the PC 40. In this way, the PC 40 obtains the plural images produced by the imager 22 which captures the electron diffraction patterns constructed from the electron beam passing through the positions on the sample S.

The PC 40 (processing section) finds the signal intensity at each position on the sample S by integrating the intensity value of each pixel within the set integration region $I_{BF\text{-}STEM}$ for each of the obtained images (step S106). Then, the PC 40 (processing section) generates a bright-field STEM image on the basis of the signal intensities at the positions on the sample S (step S108).

Whenever the imager 22 captures the electron diffraction pattern at each position on the sample S, the PC 40 may find the intensity value by integrating the integration value at each pixel within the set integration region and cause the signal intensity to be reflected in the STEM image. That is, capturing of the electron diffraction pattern and generation of a STEM image may be carried out in parallel. Alternatively, after the imager 22 captures the electron diffraction pattern at each position on the sample S and the PC 40 obtains all the images necessary to generate a STEM image, the PC 40 may integrate the intensity value of each pixel within the set integration region, find the signal intensity, and generate the STEM image.

The STEM image can be generated because of the operational sequence described thus far. The PC 40 performs processing to display the obtained STEM image on the display unit of the PC 40.

In the foregoing example, the PC 40 generates a bright-field (BF) STEM image. Annular bright-field (ABF) STEM image, differential phase contrast (DPC) STEM image, and annular differential phase (ADP) STEM image can be generated by similar processing.

The scanning transmission electron microscope 100 has the following features. In the scanning transmission electron microscope 100, the PC 40 (processing section) operates to make the imager 22 capture an electron diffraction pattern formed by the electron beam passing through each position on the sample S by scanning of the electron beam so that plural images are produced, to integrate the intensity of each pixel within an integration region set based on the diameter of the transmission disk for each of the produced plural images to thereby find the signal intensity at each position on the sample S, and to generate a STEM image on the basis of the signal intensities at the positions on the sample S. Therefore, in the scanning transmission electron microscope 100, various types of STEM images can be generated according to the purpose of observation or analysis and depending on the integration region. Consequently, the scanning transmission electron microscope 100 can produce plural types of STEM images using only one detector (imager 22).

Furthermore, the scanning transmission electron microscope 100 can generate STEM images while setting the integration region at will. Therefore, greater latitude is allowed in producing STEM images. For example, in the prior art scanning transmission electron microscope, in order to obtain a novel type of STEM image, a new detector must be prepared. In the scanning transmission electron microscope 100, a new type of STEM image can be obtained simply by setting a corresponding integration region.

Furthermore, in the above description, during processing for generating a STEM image, one type of STEM image is generated by setting one integration region for a respective one of plural images captured by the imager 22 and finding the signal intensity. The present invention is not restricted to this method. The scanning transmission electron microscope 100 can generate plural types of STEM images simultaneously by setting plural integration regions for the plural images captured by the imager 22 and finding the signal intensity for each integration region.

Specifically, during the processing for finding the signal intensity at each position on the sample S, the PC 40 (processing section) finds the signal intensity at each position on the sample S for each of the set integration regions. At this time, the integration regions may overlap with each other on the image. For example, the integration region $I_{ABF\text{-}STEM}$ shown in FIG. 6 and the integration regions $I_{DPC\text{-}STEM}$ (+) and $I_{DPC\text{-}STEM}$ (−) shown in FIG. 7 overlap with each other on the image but can be set at the same time. The PC 40 (processing section) generates plural STEM images corresponding to the plural integration regions during the processing for generating STEM images.

For example, in the prior art scanning transmission electron microscope, when plural types of STEM images are obtained at the same time, corresponding plural detectors must be prepared. Furthermore, their optical signal detecting portions must not overlap with each other. On the other hand, in the scanning transmission electron microscope 100, as noted above, plural types of STEM images can be generated at the same time using only one detector (imager 22). In addition, the microscope 100 can generate, at one time, a combination of STEM images which require overlap of optical signal detecting portions.

2. Second Embodiment 2.1. Scanning Transmission Electron Microscope

Figure 11:
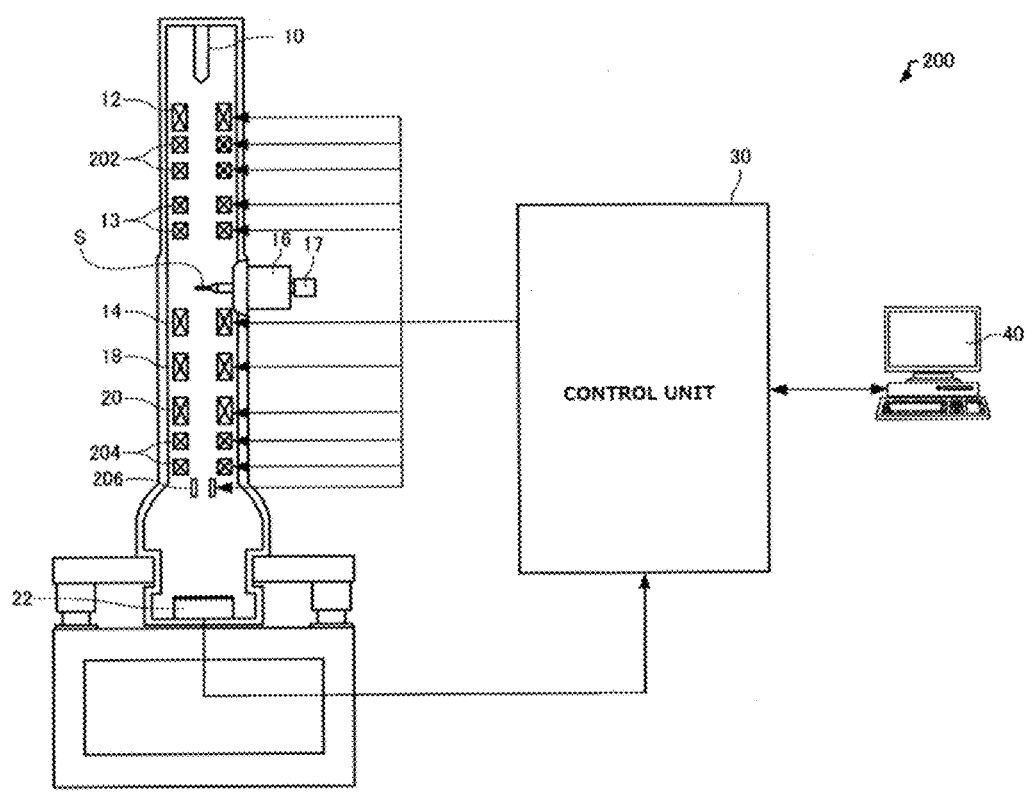
FIG. 11 is a schematic diagram, partly in cross section, of a scanning transmission electron microscope associated with a second embodiment.

A scanning transmission electron microscope associated with a second embodiment is next described by referring to FIG. 11, which schematically shows the scanning transmission electron microscope, 200, associated with the second embodiment. Those component parts of the scanning transmission electron microscope 200 which are similar in function to their respective counterparts of the scanning transmission electron microscope 100 associated with the first embodiment are hereinafter indicated by the same reference numerals as in the above-referenced figures and a detailed description thereof is omitted.

The scanning transmission electron microscope 200 associated with the second embodiment can generate STEM images in the same way as the above-described scanning transmission electron microscope 100. Furthermore, the microscope 200 can perform an axial alignment to bring the transmission disk into the center of the image captured by the imager 22.

As shown in FIG. 11, the scanning transmission electron microscope 200 is configured including tilt coils 202 (one example of first deflector), descan coils 204, and a second deflector 206. In the microscope 200, the PC 40 that is one example of processing section controls the tilt coils 202 and the second deflector 206 to bring the transmission disk present within an electron diffraction pattern into the center of the image captured by the imager 22, thus achieving an axial alignment.

The tilt coils 202 deflect the electron beam in a two-dimensional manner. The azimuthal angle and incident angle of the electron beam incident on the sample S can be modified by deflecting the electron beam using the tilt coils 202. As a result, at least one of the azimuthal angle and the incident angle of the electron beam impinging on the sample S can be scanned angularly. Thus, rocking of the beam is carried out.

The electrons transmitted through the sample S are scanned in two dimensions by the descan coils 204. The descan coils 204 are used to swing the electron beam back to the optical axis of the optical system of the scanning transmission electron microscope 200 by modifying the azimuthal angle and the incident angle of the beam with the tilt coils 202.

The electrons transmitted through the sample S are deflected in two dimensions by the second deflector 206. The deflector 206 is disposed ahead of the imager 22 (i.e., on the upstream side of the imager 22 relative to the direction of the flow of the electron beam). The electron beam can be made to hit the photosensitive area of the imager 22 at a desired position by deflecting the beam by means of the second deflector 206. For example, the deflector 206 is an electrostatic deflector that deflects electrons by an electric field. Alternatively, the second deflector 206 may be an electromagnetic deflector that deflects electrons by a magnetic field.

The PC 40 (processing section) performs processing to perform an axial alignment, for example, prior to the processing for generation of STEM images. The axial alignment makes it possible to bring the transmission disk into the center of the image captured by the imager 22.

2.2. Method of Axial Alignment

A method of axial alignment associated with the present embodiment is first described. This method of axial alignment involves the steps of: scanning the azimuthal angle of an electron beam incident on the sample S to obtain electron diffraction patterns at different values of the azimuthal angle and capturing images each containing transmission and diffraction disks in a respective one of the electron diffraction patterns by the use of the imager 22; accumulating the images to produce an accumulation image; extracting a transmission disk from the accumulation image; and deflecting the electron beam incident on the imager 22 such that the extracted transmission disk is brought to the center of the image captured by the imager 22.

Figure 12:
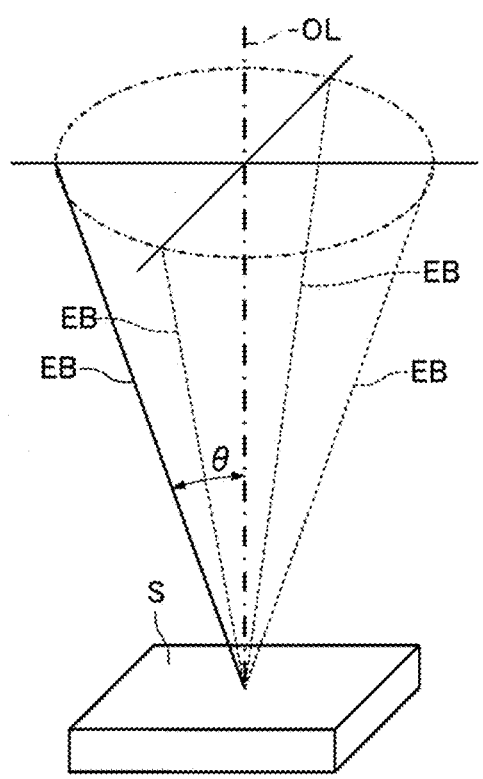
FIG. 12 is a perspective diagram schematically illustrating the manner in which the azimuthal angle of an electron beam incident on a sample is being scanned.
Figure 13:
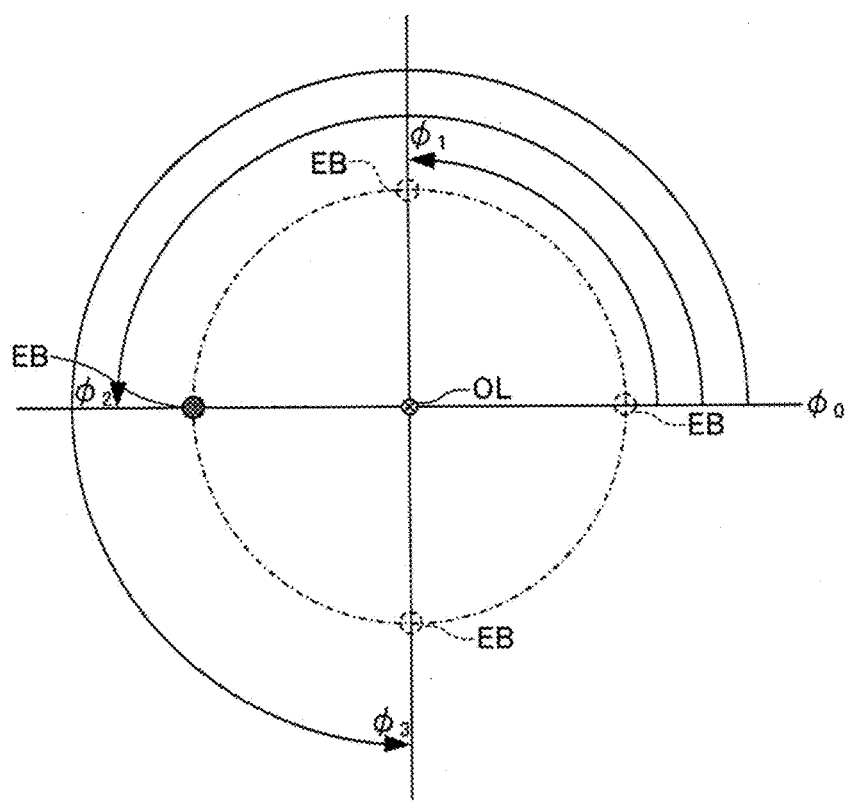
FIG. 13 is a schematic diagram illustrating the manner in which the azimuthal angle of the beam incident on the sample is being scanned.

FIGS. 12 and 13 schematically illustrate the manner in which the azimuthal angle $\phi$ of the electron beam EB incident on the sample S is being scanned. FIG. 13 is a diagram as viewed from a direction along the optical axis OL.

As shown in FIGS. 12 and 13, by deflecting the electron beam EB by the tilt coils 202, the azimuthal angle $\phi$ of the electron beam EB incident on the sample S can be varied (scanned) while maintaining the position on the sample S hit by the beam EB fixed. In the illustrated example, the azimuthal angle $\phi$ is varied four times to $\phi_0$, $\phi_1$, $\phi_2$, and $\phi_3$ in turn. If the azimuthal angle $\phi_0=0°$, it follows that $\phi_1=90°$, $\phi_2=180°$, $\phi_3=270°$. That is, the azimuthal angle $\phi$ is varied in increments of 90°.

In the illustrated example, the azimuthal angle $\phi$ of the electron beam EB is varied four times in increments of 90°. The present invention is not restricted to this method. For example, the azimuthal angle $\phi$ of the electron beam EB may be varied 8 times in increments of 45°. The angle may also be varied 12 times in increments of 30°. If the azimuthal angle $\phi$ of the electron beam EB is varied a greater number of times, the transmission disk can be extracted from the accumulation image with greater ease.

Here, only the azimuthal angle $\phi$ is varied while the incident angle $\theta$ of the electron beam EB incident on the sample S is kept constant. In the illustrated example, the incident position of the electron beam EB is the point of intersection of the electron beam EB and the optical axis OL on the sample S. The incident angle $\theta$ may be scanned as well as the azimuthal angle $\phi$.

Figure 14:
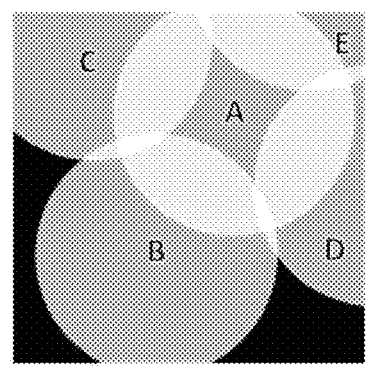
FIG. 14 is a schematic diagram of an image containing transmitted and diffracted waves within an electron diffraction pattern formed when an electron beam is made to impinge on a sample along an optical axis.
Figure 15:
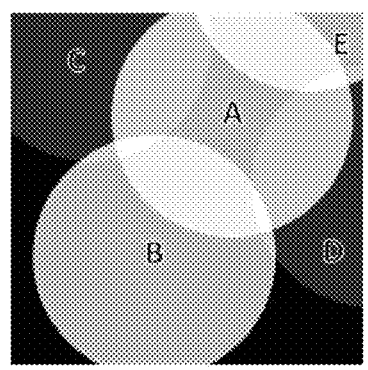
FIG. 15 is a schematic diagram of an image containing transmitted and diffracted waves within an electron diffraction pattern formed when the electron beam incident on the sample is tilted.

FIG. 14 schematically illustrates an image containing transmitted and diffracted waves in an electron diffraction pattern when the electron beam is made to impinge on the sample S along the optical axis OL. FIG. 15 schematically illustrates an image containing transmitted and diffracted waves in the electron diffraction pattern when the electron beam incident on the sample S is tilted by the tilt coils 202.

In FIGS. 14 and 15, the sample S is crystalline. In FIG. 14, the sample stage 16 is so adjusted that a crystal zone axis of the sample S extends along the optical axis OL. That is, in FIG. 14, the electron beam impinges on the sample S along the crystal zone axis of the sample S. In FIG. 15, the beam impinges on the sample S not along the crystal zone axis of the sample S. That is, the beam impinges on the sample S at an angle off the crystal zone axis.

When the conically converged electron beam impinges on the sample S, an electron diffraction pattern in which transmitted and diffracted waves are spread like disks is formed in the back focal plane of the objective lens 14. The image containing the transmitted and diffracted waves in the electron diffraction pattern shown in FIGS. 14 and 15 is observed to have disks A, B, C, D, and E. The disk A is an image of a transmitted wave (transmission disk). The disks B, C, D, and E are images of diffracted waves (diffraction disks). FIG. 14 shows a case in which the disks A, B, C, D, and E are substantially identical to each other in intensity.

In most cases, a transmission disk is greater in intensity than a diffraction disk. However, in some cases, the intensity of a diffraction disk is approximately equal to or greater than that of a transmission disk.

When an electron diffraction pattern has been obtained as shown in FIG. 14, if the electron beam incident on the sample S is tilted (e.g., the beam is tilted towards the disks C and D), then the beam hitting the sample S is tilted off the crystal zone axis and, therefore, the disks C and D decrease in intensity as shown in FIG. 15. Furthermore, when an electron diffraction pattern has been obtained as shown in FIG. 14, if the beam is tilted towards the disks B and E, the disks B and E similarly decrease in intensity in a manner not illustrated. In this way, the intensities of the diffraction disks B, C, D, and E vary according to the azimuthal angle $\phi$ of the electron beam incident on the sample S. Meanwhile, with respect to the transmission disk A, its intensity does not vary greatly if the azimuthal angle $\phi$ of the electron beam hitting the sample S is changed. Rather, the intensity of the disk A varies to a lesser extent than the diffraction disks B, C, D, and E.

Figure 16:
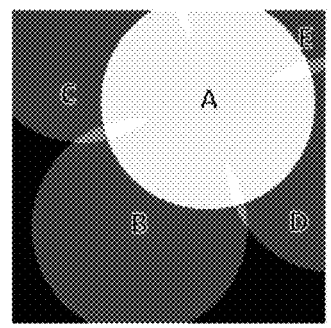
FIG. 16 is a schematic diagram of an image produced when the azimuthal angle of the electron beam incident on the sample is scanned.

FIG. 16 schematically illustrates an image obtained by scanning the azimuthal angle ϕ of the electron beam incident on the sample S. It can be said that the image (which may be hereinafter referred to as the accumulation image) of FIG. 16 has been produced by accumulation of electron diffraction patterns at various values of the azimuthal angle ϕ.

By accumulating images obtained by scanning the azimuthal angle ϕ of the electron beam, the intensities of the diffraction disks B, C, D, and E decrease in comparison to the intensity of the transmission disk A. Therefore, in the accumulation image shown in FIG. 16, the transmission disk A has the highest intensity among the disks A, B, C, D, and E in the electron diffraction pattern.

The accumulation image shown in FIG. 16 can be obtained by scanning the azimuthal angle ϕ of the electron beam, capturing electron diffraction patterns at different values of the azimuthal angle ϕ by the imager 22, and accumulating the captured images. Furthermore, the accumulation image of FIG. 16 can be obtained by making an exposure with the imager 22 while scanning the azimuthal angle ϕ of the electron beam.

In the examples shown in FIGS. 12 and 13, the azimuthal angle ϕ is varied to four directions (azimuthal angle $\phi=\phi_0$, $\phi_1$, $\phi_2$, and $\phi_3$) by the tilt coils 202 and so the imager 22 captures four images. An accumulation image is generated by accumulating the four images. As the number of accumulated images which are produced at different values of the azimuthal angle ϕ is increased, the intensity of the transmission disk A increases in comparison to the intensities of the diffraction disks B, C, D, and E and thus the transmission disk A can be extracted with greater ease. Accordingly, it is desirable to increase the number of accumulated images as much as possible.

As described previously, in an accumulation image, a disk having the highest intensity among plural disks contained in the accumulation image forms a transmission disk. Therefore, the transmission disk can be extracted by extracting the disk of the highest intensity from the plural disks contained in the accumulation image.

Figure 17:
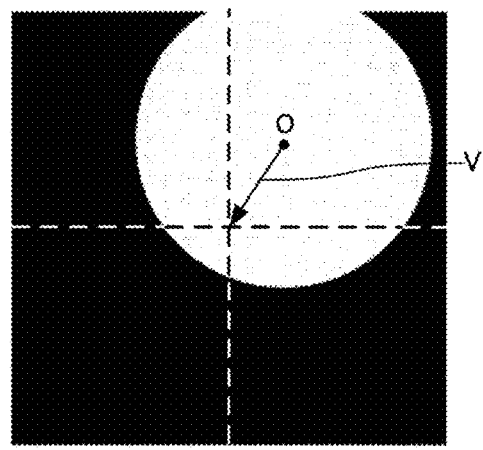
FIG. 17 shows an image produced by binarizing an accumulation image.

FIG. 17 shows an image obtained by binarizing the accumulation image shown in FIG. 16. In FIG. 17, the point of intersection of broken lines intersecting with each other at right angles indicates the center of the image.

A disk having the highest intensity (i.e., the transmission disk A) can be extracted from plural images contained in the accumulation image shown in FIG. 16 by binarizing the accumulation image with a given threshold value. This threshold value is set, for example, between a minimum intensity of pixel in the transmission disk A and a maximum intensity of pixel in the diffraction disks B, C, D, and E. The transmission disk A can be extracted with higher accuracy by using edge detection in addition to the binarization of the image.

Referring still to FIG. 17 showing the binary image having the extracted transmission disk A, a correction vector V is obtained by calculating the position of the center of gravity O of the image and calculating a vector extending from the position of the center of gravity O to the center of the image. Based on the correction vector V, the amount of current through the second deflector 206 is controlled to deflect the electron beam. The relationship between the amount of current through the second deflector 206 and the amount of deflection of the electron beam is precalibrated.

Figure 18:
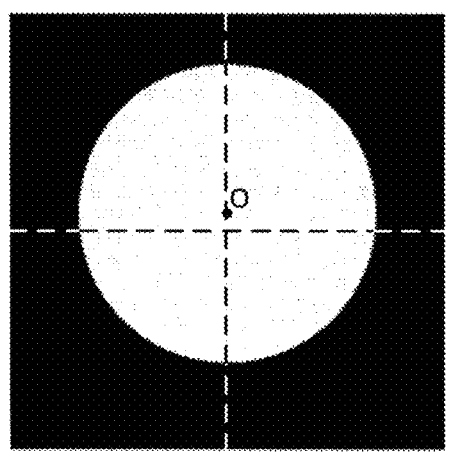
FIG. 18 shows an image produced by deflecting the electron beam on the basis of a correction vector so as to move a transmission disk.

FIG. 18 shows an image obtained after moving the transmission disk A by deflecting the electron beam based on the correction vector V. In the image of FIG. 18 where the transmission disk A has been already moved, the center of gravity O is not located at the center of the image for the following reason. In the image of FIG. 16 where the transmission disk A is not yet moved, a top portion of the disk A sticks out of the image and thus a part of the transmission disk A is missing. However, the transmission disk A can be brought into the center of the image by repeating the above-described processing.

(2) Operation of Scanning Transmission Electron Microscope

Figure 19:
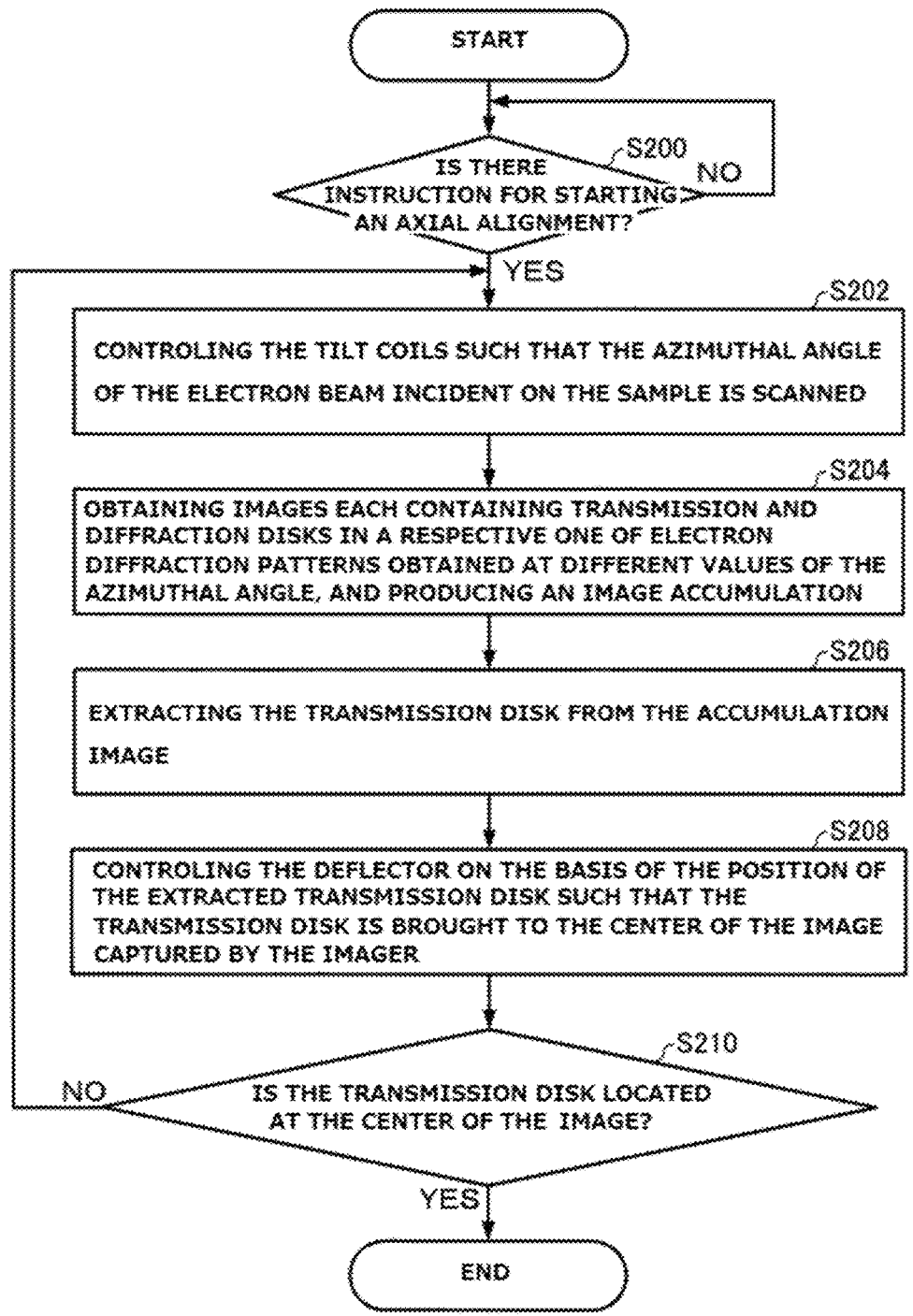
FIG. 19 is a flowchart illustrating one example of operational sequence of the scanning transmission electron microscope of FIG. 11.

The operation of the scanning transmission electron microscope associated with the second embodiment is next described. Here, the operation of the scanning transmission electron microscope 200 to perform an axial alignment is described. FIG. 19 is a flowchart illustrating one example of operational sequence of the microscope 200 associated with the second embodiment.

First, the PC 40 (processing section) makes a decision as to whether the user has issued an instruction for starting an axial alignment (step S200). The PC 40 determines that the user has issued such an instruction for starting an axial alignment, for example, if the user has performed a manipulation for starting the axial alignment using an axial alignment starting button, the keyboard, a GUI, or the like.

If the decision at step S200 is YES, indicating that an instruction for starting an axial alignment has been issued, the PC 40 (processing section) controls the tilt coils 202 such that the azimuthal angle ϕ of the electron beam incident on the sample S is scanned (step S202). Whenever the azimuthal angle ϕ of the electron beam incident on the sample S is varied by the tilt coils 202, the imager 22 captures an image containing transmission and diffraction disks in an electron diffraction pattern.

The PC 40 (processing section) obtains images each containing transmission and diffraction disks in a respective one of electron diffraction patterns obtained at different values of the azimuthal angle ϕ, the images being captured by the imager 22. The PC 40 accumulates these images and produces an integration image (step S204).

Then, the PC 40 (processing section) extracts the transmission disk from the accumulation image (step S206). Specifically, the PC 40 extracts the disk of the highest intensity from the plural disks contained in the accumulation image. More specifically, the PC 40 binarizes the accumulation image using a given threshold value so as to produce a binary image and extracts the disk of the highest intensity from the plural disks. Consequently, the transmission disk can be extracted from the accumulation image.

Then, the PC 40 (processing section) controls the second deflector 206 on the basis of the position of the extracted transmission disk such that the transmission disk is brought to the center of the image captured by the imager 22 (step S208).

The PC 40 computes the position of the center of gravity O of the binary image, for example, and computes the correction vector V extending to the center of the binary image from the position of the center of gravity O (see FIG. 17). The PC 40 then controls the amount of current supplied to the second deflector 206 on the basis of the correction vector V. Consequently, the position of the diffraction pattern in the image captured by the imager 22 moves.

The PC 40 (processing section) then makes a decision as to whether the transmission disk in the image captured by the imager 22 is located at the center of the image (step S210). If the magnitude of the correction vector V computed at step S108 is equal to or less than a given value, for example, the PC 40 determines that the transmission disk is located at the center of the image.

If the decision at step S210 is negative (NO) indicating that the transmission disk is not located at the center of the image captured by the imager 22, the PC 40 (processing section) returns to step S202 and performs the processing of steps S202, S204, S206, S208, and S210. The PC 40 repeatedly performs the processing of these steps S202-S210 until it is determined that the transmission disk is located at the center of the image captured by the imager 22.

If the decision at step S210 is affirmative (YES) indicating that the transmission disk is located at the center of the image captured by the imager 22, the PC 40 (processing section) ends the processing subroutine.

In the above description, the imager 22 captures an image containing transmission and diffraction disks in an electron diffraction pattern whenever the azimuthal angle ϕ of the electron beam incident on the sample S is varied, and the PC 40 performs step S204 to accumulate such images and obtain an accumulation image. The present invention is not restricted to this method. For example, while the azimuthal angle ϕ of the electron beam is being scanned, the imager 22 makes an exposure and thereby captures an accumulation image. The PC 40 accepts and obtains the accumulation image.

The scanning transmission electron microscope 200 performs processing to generate STEM images after the above-described axial alignment. The scanning transmission electron microscope 200 has the following features. In the scanning transmission electron microscope 200 associated with the present embodiment, the PC 40 (processing section) operates to control the tilt coils 202 such that the azimuthal angle ϕ of the electron beam incident on the sample S is scanned, to obtain an accumulation image by accumulating images each containing transmitted and diffracted waves in a respective one of electron diffraction patterns produced at different values of the azimuthal angle ϕ, to extract a transmission disk from the accumulation image, and to control the second deflector 206 on the basis of the position of the extracted transmission disk such that the transmission disk is placed at the center of the image captured by the imager 22. Therefore, in the electron microscope 200, an axial alignment can be performed automatically. Furthermore, in the microscope 200, by performing an axial alignment in advance to bring the transmission disk into the center of the image, the diameter of the transmission disk can be found easily. Consequently, the microscope 200 can easily generate STEM images.

It is to be understood that the present invention is not restricted to the foregoing embodiments and that the invention can be practiced in variously modified forms without departing from the gist of the invention.

For example, in one example of the above-described first embodiment, the diameter of the transmission disk A is measured by taking an intensity profile along a straight line L passing through the center of the transmission disk shown in FIG. 2. In another example, the measurement is made using a Hough transform. The method of measuring the diameter of the transmission disk A is not restricted thereto. For example, as shown in FIG. 20, the diameter of the transmission disk A can be measured by taking an intensity profile along plural straight lines L which extend through the center of the transmission disk A but which lie in different directions.

Figure 20:
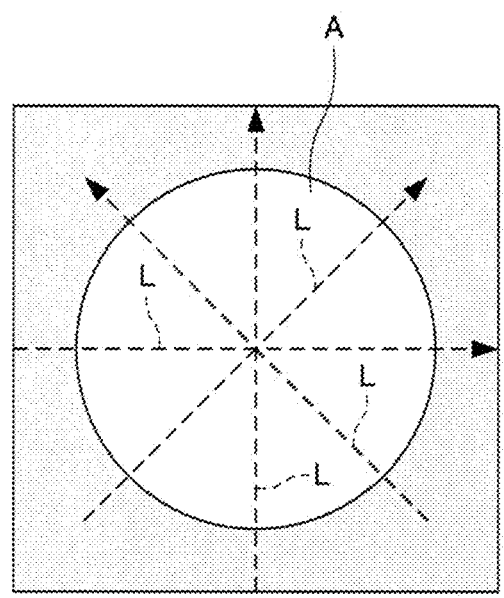
FIG. 20 is a diagram illustrating a method according to a modified embodiment to measure the diameter of a transmission disk.
Figure 21:
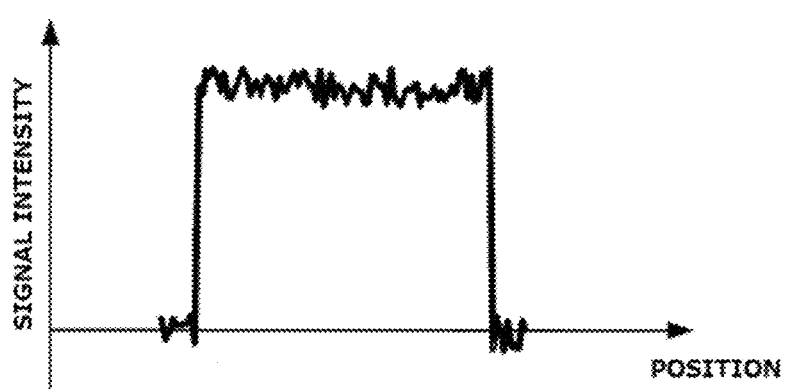
FIG. 21 is a graph illustrating the result of an accumulation of intensity profiles taken along plural straight lines which pass through the center of a transmission disk and which extend in different directions.
Figure 22:
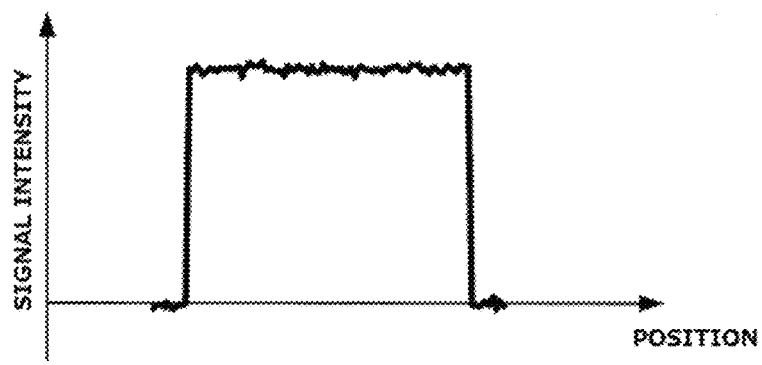
FIG. 22 is a graph showing the result of smoothing of an accumulated intensity profile.
Figure 23:
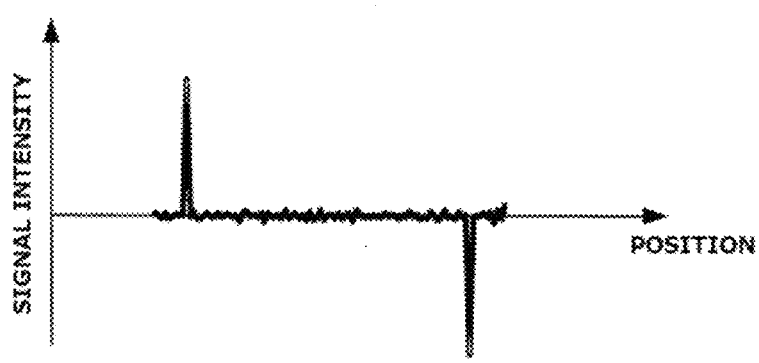
FIG. 23 is a graph showing the result of a differentiation of the smoothed intensity profile.

FIG. 21 is a graph illustrating the result of an accumulation process on the intensity profile along the plural straight lines L which pass through the center of the transmission disk A shown in FIG. 20 but which extend in different directions. FIG. 22 is a graph illustrating the result of smoothing of the accumulated intensity profile shown in FIG. 21. FIG. 23 is a graph illustrating the result of a differentiation of the smoothed intensity profile shown in FIG. 22.

Referring first to FIG. 20, a plurality of intensity profiles along plural straight lines L extending in different directions is obtained. The obtained intensity profiles are accumulated. As a result, the intensity profile shown in FIG. 21 is obtained.

Then, the accumulated intensity profile shown in FIG. 21 is smoothed. As a result, the intensity profile shown in FIG. 22 is obtained.

Then, the smoothed intensity profile shown in FIG. 22 is differentiated. As shown in FIG. 23, in the differentiated intensity profile, the signal intensity increases at the edges of the transmission disk A. Therefore, the edges of the transmission disk A can be detected and thus the diameter of the transmission disk A can be found.

According to the present modification, when the diameter of the transmission disk A is measured, plural intensity profiles extending along the plural straight lines L lying in different directions are obtained and so the diameter of the transmission disk A can be found with higher accuracy. Furthermore, according to the present modification, the accumulated intensity profile is smoothed and, therefore, the accuracy at which the edges of the transmission disk A are detected can be enhanced.

It is to be noted that the above-described embodiments and modification are merely exemplary and that the invention is not restricted thereto. For example, the embodiments and modification may be appropriately combined.

The present invention embraces configurations (e.g., configurations identical in function, method, and results or identical in purpose and advantageous effects) which are substantially identical to the configurations described in any one of the above embodiments. Furthermore, the invention embraces configurations which are similar to the configurations described in any one of the above embodiments except that their nonessential portions have been replaced. Additionally, the invention embraces configurations which are identical in advantageous effects to, or which can achieve the same object as, the configurations described in any one of the above embodiments. Further, the invention embraces configurations which are similar to the configurations described in any one of the above embodiments except that a well-known technique is added.

Having thus described my invention with the detail and particularity required by the Patent Laws, what is desired protected by Letters Patent is set forth in the following claims.

The invention claimed is:

1. A scanning transmission electron microscope adapted to produce scanned images by scanning an electron beam over a sample, said scanning transmission electron microscope comprising:
   an electron source for emitting an electron beam;
   a scanning deflector for scanning the emitted electron beam over the sample;
   an objective lens for converging the electron beam emitted from the electron source;
   an imager placed at a back focal plane of the objective lens or at a plane conjugate with the back focal plane; and
   a scanned image generator for generating the scanned images on the basis of images captured by the imager,
   wherein the scanned image generator operates to form electron diffraction patterns from the electron beam passing through positions on the sample by scanning of the electron beam, to capture the electron diffraction patterns by the imager so that plural images are produced, to integrate the intensity of each pixel over an integration region that is set based on the size of an image of a transmitted wave within a respective one of the produced images such that the signal intensity at each position on the sample is found for each of the produced images, and to generate the scanned images on the basis of the signal intensities at the positions on the sample, wherein said scanned image generator operates to measure the size of the image of said transmitted wave from the image captured by said imager and to set said integration region on the basis of the measured size of the image of the transmitted wave.

2. The scanning transmission electron microscope as set forth in claim 1, wherein the image of said transmitted wave in the image captured by said imager appears as a disk, and wherein the size of the image of the transmitted wave is the diameter of the disk.

3. The scanning transmission electron microscope as set forth in claim 1, wherein during the operation for finding the signal intensity at each position on the sample, said scanned image generator finds the signal intensity at each position on the sample for each of the plural set integration regions, and where during the operation for generating the scanned images, the scanned image generator generates the scanned images corresponding to the plural integration regions.

4. The scanning transmission electron microscope as set forth in claim 1, wherein said integration regions are inside the image of said transmitted wave and are circular regions whose centers lie at the center of the image of the transmitted wave.

5. The scanning transmission electron microscope as set forth in claim 1, wherein said integration regions are inside the image of said transmitted wave and are annular regions whose centers lie at the center of the image of the transmitted wave.

6. The scanning transmission electron microscope as set forth in claim 1, wherein said integration regions are outside and surround the image of said transmitted wave and are annular regions whose centers lie at the center of the image of the transmitted wave.

7. The scanning transmission electron microscope as set forth in claim 1, wherein said integration regions are inside the image of said transmitted wave and are two regions which are symmetrical with respect to the center of the image of the transmitted wave.

8. A scanning transmission electron microscope adapted to produce scanned images by scanning an electron beam over a sample, said scanning transmission electron microscope comprising:
an electron source for emitting an electron beam;
a scanning deflector for scanning the emitted electron beam over the sample;
an objective lens for converging the electron beam emitted from the electron source;
an imager placed at a back focal plane of the objective lens or at a plane conjugate with the back focal plane; and
a scanned image generator for generating the scanned images on the basis of images captured by the imager, wherein the scanned image generator operates to form electron diffraction patterns from the electron beam passing through positions on the sample by scanning of the electron beam, to capture the electron diffraction patterns by the imager so that plural images are produced, to integrate the intensity of each pixel over an integration region that is set based on the size of an image of a transmitted wave within a respective one of the produced images such that the signal intensity at each position on the sample is found for each of the produced images, and to generate the scanned images on the basis of the signal intensities at the positions on the sample,
wherein said scanning transmission electron microscope, further comprises:
a first deflector for deflecting the electron beam incident on said sample;
a second deflector for deflecting the electron beam incident on said imager; and
a processor for controlling the first and second deflectors, wherein the processor operates to control the first deflector such that an azimuthal angle of the electron beam incident on the sample is scanned, to obtain an accumulation image consisting of an accumulation of images each containing a transmitted wave and diffracted waves in a respective one of electron diffraction patterns produced at different values of the azimuthal angle, to extract the image of the transmitted wave from the accumulation image, and to control the second deflector on the basis of the position of the extracted image of the transmitted wave such that the image of the transmitted wave is placed at the center of the image captured by the imager.

9. The scanning transmission electron microscope as set forth in claim 8, wherein the image of said transmitted wave in the image captured by said imager appears as a disk, and wherein the size of the image of the transmitted wave is the diameter of the disk.

10. The scanning transmission electron microscope as set forth in claim 8, wherein during the operation for finding the signal intensity at each position on the sample, said scanned image generator finds the signal intensity at each position on the sample for each of the plural set integration regions, and where during the operation for generating the scanned images, the scanned image generator generates the scanned images corresponding to the plural integration regions.

11. The scanning transmission electron microscope as set forth in claim 8, wherein said integration regions are inside the image of said transmitted wave and are circular regions whose centers lie at the center of the image of the transmitted wave.

12. The scanning transmission electron microscope as set forth in claim 8, wherein said integration regions are inside the image of said transmitted wave and are annular regions whose centers lie at the center of the image of the transmitted wave.

13. The scanning transmission electron microscope as set forth in claim 8, wherein said integration regions are outside and surround the image of said transmitted wave and are annular regions whose centers lie at the center of the image of the transmitted wave.

14. The scanning transmission electron microscope as set forth in claim 8, wherein said integration regions are inside the image of said transmitted wave and are two regions which are symmetrical with respect to the center of the image of the transmitted wave.

* * * * *